United States Patent
Papkovsky et al.

(10) Patent No.: US 12,181,414 B2
(45) Date of Patent: *Dec. 31, 2024

(54) METHOD AND PROBE FOR MONITORING OXYGEN STATUS IN LIVE MAMMALIAN CELLS

(71) Applicant: UNIVERSITY COLLEGE CORK, NATIONAL UNIVERSITY OF IRELAND, CORK, Cork (IE)

(72) Inventors: Dmitri Papkovsky, County Cork (IE); Andreas Fercher, Cork (IE); Ingo Klimant, Labuch (AT); Sergey Borisov, Graz (AT); Alexander Zhdanov, Cork (IE)

(73) Assignee: UNIVERSITY COLLEGE CORK, NATIONAL UNIVERSITY OF IRELAND, CORK, Cork (IE)

(*) Notice: Subject to any disclaimer, the term of this patent is extended or adjusted under 35 U.S.C. 154(b) by 502 days.

This patent is subject to a terminal disclaimer.

(21) Appl. No.: 16/704,587

(22) Filed: Dec. 5, 2019

(65) Prior Publication Data

US 2020/0173927 A1 Jun. 4, 2020

Related U.S. Application Data

(63) Continuation of application No. 13/879,933, filed as application No. PCT/EP2010/066006 on Oct. 22, 2010, now Pat. No. 10,508,992.

(51) Int. Cl.
| | |
|---|---|
| *G01N 33/58* | (2006.01) |
| *B82Y 30/00* | (2011.01) |
| *G01N 21/64* | (2006.01) |
| *G01N 33/50* | (2006.01) |
| *G01N 33/84* | (2006.01) |

(52) U.S. Cl.
CPC .......... *G01N 21/6486* (2013.01); *B82Y 30/00* (2013.01); *G01N 33/5005* (2013.01); *G01N 33/5008* (2013.01); *G01N 33/582* (2013.01); *G01N 33/587* (2013.01); *G01N 33/84* (2013.01)

(58) Field of Classification Search
CPC .......... G01N 21/6486; G01N 33/5005; G01N 33/587; G01N 33/84; G01N 33/5008; G01N 33/582; B82Y 30/00
See application file for complete search history.

(56) References Cited

U.S. PATENT DOCUMENTS

| | | | | |
|---|---|---|---|---|
| 5,128,319 | A | | 7/1992 | Arlinghaus |
| 5,462,880 | A | * | 10/1995 | Kane ............... G01N 21/7703 422/82.07 |
| 10,508,992 | B2 | * | 12/2019 | Papkovsky ........ G01N 21/6486 |
| 2020/0173927 | A1 | * | 6/2020 | Papkovsky .......... G01N 33/582 |

FOREIGN PATENT DOCUMENTS

| | | | |
|---|---|---|---|
| WO | WO-2006119087 A2 | * 11/2006 | ......... G01N 21/6428 |
| WO | 2012052068 A1 | 4/2012 | |
| WO | 2018206746 A1 | 11/2018 | |

OTHER PUBLICATIONS

Borisov et al. Precipitation as a simple and versatile method for preparation of optical nanochemosensors. Talanta 2009. Available online Jun. 2009. 79: 1322-1330. (Year: 2009).*

Papkovsky et al. Methods in optical oxygen sensing: protocols and critical analysis. Methods in Enzymology. 2004, 381: 715-735. (Year: 2004).*

O'Riordan et al. Analysis of intracellular oxygen and metabolic responses of mammalian cells by time-resolved fluorometry. Anal. Chem. 2007, vol. 79, pp. 9414-9419. (Year: 2007).*

Koo Lee et al. Optic nanoparticle sensors for quantitative intracellular imaging. Wiley Interdiscip Rev Nanomed Nanobiotechnol 2009, vol. 1, pp. 98-110. (Year: 2009).*

Gargouri et al. Optimization of a new non-viral vector for transfection: Eudragit nanoparticles for the delivery of a DNA plasmid. Technology in Cancer Research & Treatment, 2009, vol. 8, No. 6, pp. 433-443. (Year: 2009).*

Zhdanov et al., Monitoring of cell oxygenation and responses to metabolic stimulation by intracellular oxygen sensing technique, Integrative Biology, Integrative Biology, Sep. 2010, 443-451, vol. 2 issue 9, The Royal Society of Chemistry, doi: 10.1039/c0ib00021c.

Fercher et al., "Intracellular 0 2 Sensing Probe Based on Cell-Penetrating Phosphorescent Nanoparticles" ACS Nano (2011) vol. 5, No. 7, pp. 5499-5508.

Kondrashina et al., "A Phosphorescent Nanoparticle-Based Probe for Sensing and Imaging of (Intra)Cellular Oxygen in Multiple Detection Modalities" Advanced Functional Materials (2012) vol. 22, pp. 4931-4939.

Dmitriev et al., "Imaging oxygen in neural cell and tissue models by means of anionic cell-permeable phosphorescent nanoparticles" Cellular and Molecular Life Sciences (2015) vol. 72, pp. 367-381.

Dmitriev et al., "Versatile Conjugated Polymer Nanoparticles for High-Resolution 02 Imaging in Cells and 3D Tissue Models" ACS Nano (2015) vol. 9, No. 5, pp. 5275-5288.

Cao et al. "Poly(decyl methacrylate)-Based Fluorescent PEBBLE Swarm Nanosensors For Measuring Dissolved Oxygen In Biosamples," The Analyst, vol. 129, No. 8 (2004): 745-750.

(Continued)

*Primary Examiner* — Shafiqul Haq
(74) *Attorney, Agent, or Firm* — K&L Gates LLP (57) ABSTRACT

A method of determining oxygen concentration, metabolic activity, and/or the effects of a test substance on the metabolic activity of a live cell sample by photoluminescence quenching technique employing a photoluminescent probe that self-loads sans any loading reagent into the cells of the cell sample. The probe comprises a plurality of polymeric particles each comprising an amphiphilic cationic polymer matrix having a hydrophobic core and a hydrophilic positively charged surface provided by quaternary amino groups, and a hydrophobic oxygen-sensitive photoluminescent dye embedded in the hydrophobic core.

11 Claims, 4 Drawing Sheets

(56) References Cited

OTHER PUBLICATIONS

Coogan et al. "Probing Intracellular Oxygen By Quenched Phosphorescence Lifetimes Of Nanoparticles Containing Polyacrylamide-Embedded [Ru(dpp(SO3Na)2)3] Cl2," Photochemical and Photobiological Sciences, vol. 9, No. 1, (2009): 103-109.

Dmitriev et al. "Intracellular Probes For Imaging Oxygen Concentration: How Good Are They?" Methods And Applications In Fluorescence; vol. 3, No. 3, 034001 (2015) 12 pages.

Dmitriev et al. "Optical Probes And Techniques For O2 measurement In Live Cells And Tissue," CMLS Cellular And Molecular Life Sciences. Birkhauser-Verlag. BA., vol. 69, No. 12 (2012): 2025-2039.

Krumm et al. "Real-Time Monitoring Of Cellular Metabolic Activity: Intracellular Oxygen," BMG Labtech; Nature Methods; vol. 13; No. 10 (2016) 2 pages.

Lee et al. "Efficient Intracellular Delivery Of Functional Proteins Using Cationic Polymer Core/Shell Nanoparticles," Biomaterials, vol. 29; No. 9 (2008): 1224-1232.

Maurer et al. "Real-Time Measurement Of Intracellular O2 In Mammalian Cells," BMG Labtech; vol. 62, No. 14 (2016) 2 pages.

Wang et al. "Self-Referenced RGB Colour Imaging Of Intracellular Oxygen," Chemical Science, vol. 2, No. 5; The Royal Society of Chemistry, Chemical Science (2011): 901-906.

Zhdanov et al. "Kinetic Analysis of Local Oxygenation and Respiratory Responses of Mammalian Cells Using Intracellular Oxygen-Sensitive Probes and Time-Resolved Fluorometry," Methods In Enzymology, vol. 542, Chapter Ten (2014): 183-207.

Zobel et al. "Evaluation Of Aminoalkylmethacrylate Nanoparticles As Colloidal Drug Carrier Systems, Part 1: Synthesis Of Monomers, Dependence Of The Physical Properties Of The Polymerization Methods," European Journal of Pharmaceuticals and Biopharmaceuticals, vol. 47, No. 3 (1999): 203-213.

* cited by examiner

METHOD AND PROBE FOR MONITORING OXYGEN STATUS IN LIVE MAMMALIAN CELLS

CROSS REFERENCE TO RELATED APPLICATIONS

This application is a continuation of U.S. patent application Ser. No. 13/879,933, filed July 8, 2013, now U.S. Pat. No. 10,508,992, which is the national phase under 35 USC 371 of International Application No. PCT/EP2010/066006, filed Oct. 22, 2010. The content of the aforementioned applications is incorporated herein in its entirety.

INTRODUCTION

The invention describes the use of photoluminescent probes for assaying oxygen levels in live mammalian cells. In particular, the invention describes photoluminescent oxygen-sensitive nanoparticles which have the ability to passively load various mammalian cells and report on local cellular oxygen levels by changing their phosphorescence characteristics.

BACKGROUND TO THE INVENTION

Quantification of $O_2$ by photoluminescence quenching is an established technique which has a number of attractive features, including reversible, non-chemical and non-invasive nature of sensing of $O_2$. This methodology is actively used in various industrial and biomedical applications where measurement of $O_2$ is required (Papkovsky D B. *Meth. Enzymol.* 2004, 381: 715-735).

Moreover, it is now recognised that in such samples the level of cell oxygenation can differ significantly from that of bulk medium. This may affect the cells and induce adaptive responses and physiologic changes. Hence there is a need to accurately monitor intracellular $O_2$ levels and local $O_2$ gradients in biological samples. Simple chemistries and measurement methodologies providing this are therefore important.

A number of photoluminescence based $O_2$-sensing probes and techniques have been described so far. Rumsey W L et al. (*Science*, 1988, v. 241(4873): 1649-51), Dunphy, I, et al. (*Anal Biochem* 2002, 310(2): 191-8), Vinogradov S A et al. (U.S. Pat. No. 5,837,865, 1998), Wilson (U.S. Pat. No. 6,395,555, 2002), Hynes, J., et al. (*J Biomol Screening*, 2003, 8(3): 264-72), Cao Y. et al. (*Analyst*, 2004, 129(8): 745-50) describe probes for the sensing and imaging of $O_2$ in systems containing live cells and tissue, and for the measurement of biological $O_2$ consumption. These techniques normally employ $O_2$-sensitive Pt- and Pd-porphyrins and some related complexes as probes, luminescence of which is quenched by $O_2$. These probes were designed primarily for extracellular use, they are essentially cell-impermeable and can not be used for probing (intra)cellular $O_2$.

Several probes including polymeric nanoparticles impregnated with oxygen-sensitive dyes (Koo Y E et al. *Anal Chem.* 2004, v. 76(9): 2498-505), 'lipobeads' (Ji J. et al. *Anal Chem.*, 2001, 73(15): 3521-7); microspheres (Schmalzlin E., et al., *Biophys. J.* 2005, 89(2): 1339); hydrophilic metalloporphyrin dye bound to albumin (Howlett R A, *J Appl Physiol.* 2007, 102(4):1456-61) were applied to sensing intracellular $O_2$ by loading the cells by microprojectile delivery, phagocytosis or microinjection (in large plant cells or skeletal muscle fibres). However, these systems have low loading efficiency, uneven distribution of the probe inside the cell, uncontrolled compartmentation and aggregation, significant cyto- and phototoxicity, they are rather complex and invasive.

Another approach to cells loading is the use special reagents which facilitate transport of $O_2$ probes from the extracellular medium (O'Riordan T. C. et al. *Anal. Chem.*, 2007 Dec. 15; 79(24):9414; Fercher a. et al.—*Anal. Bioanal. Chem.* 2010, Jan. 10, PMID: 20063150). It requires additional reagents and equipment, depends on the probe, cell, medium type and other conditions. In many cases, such loading is low, cell-specific and stressful, time-consuming and not very reproducible.

$O_2$-sensitive probes with self (i.e. passive) loading capabilities were also described, for example those based on the conjugates of certain oxygen-sensitive dyes with cell-penetrating peptides (Neugebauer U, et al.—*Chem. Comm.*, 2008 (42):5307-5309, Dmitriev R I et al.—*Anal. Biochem.* 398 (2010) 24-33). These molecular probes also have drawbacks. Thus, the former probe has low brightness and short fluorescence lifetime resulting in modest sensitivity to $O_2$, and their utility in biological applications has not been demonstrated. The latter probes based on phosphorescent Pt- or Pd-coproporphyrins have modest photostability making them unusable in fluorescence oxygen imaging applications. Although these probes are brighter than Ru(II)-probes (higher molar absorptivity and emission yield), not always they provide sufficient signals for reliable and accurate $O_2$ sensing experiments. Both probe types are limited to just a few dye structures, complex synthesis procedures and high costs.

It is an object of the invention to overcome at least one of the above-referenced problems.

STATEMENTS OF INVENTION

In one aspect, the invention is based on the use of photoluminescent probes for intracellular sensing of oxygen, especially assaying intracellular oxygen concentration. The photoluminescent probe comprises a suspension of polymeric particles having an average diameter in the 20 nm to 100 nm range, formed from an amphiphilic cationic co-polymer which is oriented in the formed particle to provide a hydrophobic core and a hydrophilic shell. The probe includes a hydrophobic oxygen-sensitive photoluminescent dye such as Pt-tetrakis(pentafluorophenyl)porphine, PtPFPP embedded in the hydrophobic core of the particle, and the co-polymer includes quaternary ammonium groups which provide hydrophilic and cationic character to the particle shell. The photoluminescent probe, which in use is provided in the form of an aqueous suspension of probe, is incubated with live mammalian cells in a suitable growth medium for a period of time to allow the probe particles passively load into the cells. Oxygen can then be sensed by detecting a photoluminescent signal of the photoluminescent probe, which can be correlated with oxygen status, for example oxygen concentration or changes in oxygen concentration/levels, using existing techniques.

It has surprisingly been noted that highly efficient, reproducible probe loading of different cell types can be achieved by passive means with short incubation periods. For example for MEF cells (see FIG. 1) TR-F intensity signals (measured as described in O'Riordan T. C. etal. *Anal. Chem.*, 2007, 79(24):9414) exceeded 30,000 cps after only one hour loading. As determined from photoluminescence measurements, the concentration of the oxygen-sensitive photoluminescent dye in such loaded cells (i.e. intracellular concentration in moles dye per litre of intracellular space) normally exceeded 0.1 μM/L, being typically in the region 1-10 μM/L. This is significantly higher than for the other intracellular oxygen probes described so far. It has also been surprisingly noted that the nanoparticle photoluminescent probe is capable of providing a stable signal intensity (see FIG. 3) and reliable lifetime-based sensing of intracellular oxygen, even when located within a cell, while also demonstrating low intrinsic toxicity to the cells. Similarly, high (>30,000 cps) and stable photoluminescent signals from the loaded cells were obtained on a fluorescent microscope (measurements were carried out under the conditions described in Fercher A, et al. *Methods Mol Biol.* 2010, v. 591, p. 257-73).

Accordingly, the invention provides a method of determining oxygen status in a live mammalian cell sample by photoluminescence quenching technique, which method employs a photoluminsecent probe, the method comprising the step of:

incubating the live mammalian cell sample in a suitable growth medium with the photoluminescent probe to allow passive loading of probe;

detecting a photoluminescent signal of the photoluminescent probe from loaded cells, typically at a constant temperature (i.e 37° C.) and external gas composition (for example, normoxia—21% oxygen or hypoxia—reduced atmospheric p $O_2$); and correlating the detected photoluminescent signal to oxygen concentration in the live mammalian cells, wherein the photoluminescent probe is a polymeric particle having an average size of 20 to 100 nm and comprises an amphiphilic cationic polymer matrix having a hydrophobic core and a hydrophilic surface provided by quaternary cationic groups, and a hydrophobic oxygen-sensitive photoluminescent dye embedded in the hydrophobic core. The photoluminescent probe is generally employed in the form of an aqueous suspension of probe having a working concentration of 0.1 to 100 μg/ml.

The method of the invention is generally capable of providing high loading efficiency (i.e. intracellular probe concentration of at least 0.1 micromole/L using the measurement technique described in O'Riordan T. C. et al.).

The method of the invention is suitably capable of providing high photoluminescence intensity signal (i.e. a TR-F intensity signal of at least 30,000 cps when measured as described in O'Riordan T. C. et al).

The method of the invention is typically capable of providing a stable signal intensity (i.e. signal intensity at 24 hr post-loading which is at least 80% of signal intensity at 0 hr).

The method of the invention is generally capable of providing reliable lifetime-based sensing of intracellular oxygen.

The method of the invention is suitably capable of causing low intrinsic toxicity on the cell or cells (i.e. at least 80% cell viability 24 hr after probe loading). The term "determining oxygen status" should be understood to mean sensing the presence of oxygen, detecting changes in oxygen levels or changes in oxygen usage by the cell, and especially determining oxygen concentration. In a preferred embodiment, the invention relates to a method of determining intracellular oxygen concentration, or changes in concentration.

The term "passive loading" is an art-defined term, which is understood to mean that the probe is self-loaded into the cell without the use of an aid, for example a microinjection apparatus, or loading vectors such as for example cell-loading peptides or lipofectamine. In one aspect, it is an important feature of the invention that the photoluminescent probe is capable of efficient, fast and passive loading into live mammalian cells.

For the method of the invention, the photoluminescent probe is generally provided in the form of an aqueous suspension of probe nanoparticles, typically having a concentration of photoluminescent probe of 0.1-100 μg/ml. Such probe concentrations have been found to provide efficient passive loading at loading times as short as 1 hour.

The probe matrix is composed of an amphiplilic cationic polymer matrix. It is generally provided in the form of a co-polymer having hydrophilic and hydrophobic (lipophilic) domains, and includes quaternary cationic groups, ideally quaternary amino groups, for example quaternary ammonia groups, which in the formed nanoparticle are exposed on the surface of the nanoparticle and help provide the surface (shell) with a hydrophilic character. While the use of charged groups on the surface of probe nanoparticles is described in the literature (see for example *Biotechnol Bioeng* 2007, 96(2):318-325 which describes polystyrene beads having positively charged PEI groups grafted into the surface, where the surface charge was found to help nanoparticle assembly on cell surfaces, without passive loading), the applicant has surprisingly found that the use of use of a probe matrix formed on an amphiphilic cationic polymer having quaternary cationic groups not only allows the probe efficiently load into live cells in a passive manner, but also provides a stable signal intensity and reliable lifetime-based sensing of intracellular oxygen. The core of the formed nanoparticle has a hydrophobic character, and is suitable for embedding the hydrophobic oxygen sensitive photoluminescent dye.

In a preferred embodiment of the invention, the nanoparticle comprises a co-polymer of poly (ethylacrylate, methylmetacrylate and chloro trimethyl-ammoniethyl methacrylate) containing quaternary cationic groups. Examples of such co-polymers include Eudragit RL-100 and Eudragit RS-100. Ideally, the co-polymer comprises at least 4%, 5%, 6%, 7%, 8%, 9%, 10%, 11% or 12% quaternary cationic groups. Preferably, the groups are amino groups, ideally ammonium groups.

Generally, from 0.1% to 3.0%, 0.5% to 1.5%, and ideally 0.8% to 1.2%, (w/w) of the photoluminescent probe is oxygen sensitive photoluminescent dye.

The hydrophobic oxygen sensitive photoluminescent dye is generally selected from Pt-porphyrin, Pd-porphyrin, Pt-porphyrin-ketone or Pd-porphyrin-ketone, Pt-benzoporphyrin or Pd-benzoporphyrin, cyclometallated complex of $Ir^{3+}$, $Os^{2+}$ or $Ru^{2+}$, or close analogs or derivatives of these dyes, which dyes are typically capable of 1.5 to 15 fold quenching at ambient oxygen concentration (21 kPa or 250 μM oxygen). Example of these dyes will be well known to those skilled in the art (see for example Rumsey (Rumsey W L et al. *Science,* 1988, v. 241(4873): 1649-51), Dunphy (Dunphy, I, et al. *Anal Biochem* 2002, 310(2): 191-8), Vinogradov (Vinogradov S A et al. U.S. Pat. No. 5,837,865, 1998), Wilson (U.S. Pat. No. 6,395,555, 2002), Hynes (Hynes, J., et al. *J Biomol Screening,* 2003, 8(3): 264-72), Cao (Cao Y. et al. *Analyst,* 2004, 129(8): 745-50)), and will not be described in further detail herein. In a preferred embodiment of the invention, the hydrophobic oxygen sensitive photoluminescent dye is a PtPFPP, PtOEP or PtOEPK dye, or a close analog or derivative thereof.

The step of measuring photoluminescent signal is typically carried out at a constant temperature, as changes in temperature can affect signal strength. Thus, during signal measurement, the cells (i.e. the cell environment) are kept at a constant temperature (for example 37° C.+/−1° C.).

The cells are generally washed prior to measurement of the photoluminescent signal to remove extracellular probe.

The method of the invention may be employed to monitor oxygen status in individual cells or cell populations (for example, cells grown in-vitro or ex-vivo cell or tissue samples). The method of the invention may also be employed to monitor cell health or cell function. For example, as oxygen levels or use can function as a diagnostic variable of cellular metabolism, the method of the invention can be employed to monitor metabolism in a cell, and the effects on metabolism caused by various compounds or conditions, for example drugs, chemicals, toxins, growth factors, hormones, low molecular weight effectors of gene transcription and translations, and environmental conditions. The fact that the probe employed in the present invention exhibits little or no intrinsic toxicity to cells allows for a more accurate assessment of cellular metabolism using the method of the invention. Indeed, it is another unexpected advantage of the present invention that high loading of probe (i.e. loading that enables stable signal intensity (see FIG. 3) and reliable lifetime-based sensing of intracellular oxygen) does not result in toxicity to the cell.

Various techniques are available for measuring the photoluminescent signal, including time-resolved fluorimetry in the microsecond domain and fluorescence microscopy imaging technique. Ideally, the photoluminescence lifetime of the photoluminescent signal, or parameter related to it, is measured, although the method of the invention may also employ signal phase or intensity measurements.

In one embodiment, the method of the invention also employs ratiometric intensity based oxygen sensing or imaging. In such embodiments, the photoluminescent probe comprises an additional oxygen-insensitive dye which is used as a reference or as part of a FRET pair. Examples of such dyes include oxygen-insensitive fluorescent dyes (i.e Oregon Green 488-dextran).

The invention also provides a method of determining the metabolic status of a cell or a cell population, which method comprises a step of monitoring oxygen status of the cell or cell population according to a method of the invention, and correlating the measured oxygen status, or changes in the oxygen status, of the cell or cell population to metabolic status of the cell or cell population. Generally, the method is used to monitor metabolic activity, often in response to a stimulus, for example a drug or effector or an environmental condition. Generally, the method involves monitoring oxygen concentrations, especially changes in oxygen concentration.

Thus, in one aspect, the invention provides a method of determining the effects of a test substance or condition on the metabolic activity of a cell or cell population, the method comprising a step of stimulating a cell or cell population with the test substance or condition, and determining the metabolic activity of the cell or cell population prior to and after stimulating the cell or cell population, according to the method of the invention.

The invention also relates to a method of determining oxygen concentration in a live mammalian cell sample by photoluminescence quenching technique, which method employs a photoluminsecent probe, the method comprising the step of:

incubating the live mammalian cell sample in a suitable growth medium with the photoluminescent probe under normal physiological conditions to allow passive loading of probe;

detecting a photoluminescent signal of the photoluminescent probe from loaded cell sample at a constant temperature; and correlating the detected photoluminescent signal to oxygen concentration in the live mammalian cell sample, wherein the photoluminescent probe is a polymeric particle having an average size of 20 to 100 nm and comprising a matrix formed of a co-polymer of poly (ethylacrylate, methyl-metacrylate and chloro trimethyl-ammoniethyl methacrylate) containing quaternary ammonium groups, the matrix having a hydrophobic core and a shell characterised by the quaternary amino groups, and a hydrophobic oxygen-sensitive photoluminescent dye embedded in the hydrophobic core, wherein the dye is selected from a Pt-porphyrin, Pd-porphyrin, Pt-porphyrin-ketone or Pd-porphyrin-ketone, Pt-benzoporphyrin or Pd-benzoporphyrin, cyclometallated complex of $Ir^{3+}$, $Os^{2+}$ or $Ru^{2+}$, or close analogs or derivatives of these dyes. The method ideally comprises the steps of incubating an aqueous suspension of photoluminescent probe having a probe concentration of 1 to 10 μg/ml with the live mammalian cell under normal growth conditions at a constant temperature for a period of time from 30 minutes to 48 hours (hereafter "passive loading period").

The invention provides a method of loading a photoluminescent probe into a live mammalian cell sample, the photoluminescent probe comprising a polymeric particle having an average size of 20 to 100 nm and formed of an amphiphilic cationic polymer with a hydriophobic core and a charged shell, and an oxygen sensitive photoluminescent dye embedded in the hydrophobic core, the method comprising the steps of incubating an aqueous suspension of photoluminescent probe having a probe concentration of 1 to 10 μg/ml with the live mammalian cell sample under normal growth conditions at a constant temperature for a period of time from 30 minutes to 48 hours (hereafter "passive loading period"), wherein the photoluminescent probe is passively loaded in the cell.

As used herein, the term "passive loading period" means (and "passively load") generally mean at least 30 minutes loading period, and suitably less that 24 h, 20 h, 18 h, 16 h, 14 h, 12 h, 10 h, 9 h, 8 h, 7 h, 6 h, 5 h, 4 h, 3 h, 2 h, and 90 minutes. Thus, the passive loading periods (or passive loading) may be from 1-24 h, 1-18 h, 1-16 h, 1-14 h, 1-12 h, 1-10 h, 1-8 h, 1-6 h, 1-4 h, 1-3 h, 1-2 h, 12-24 h, 12-18 h, 12-16, 12-14 h or 12-13 h.

The invention also relates to a method of loading a photoluminescent probe into a live mammalian cell, the photoluminescent probe comprising a polymeric particle having an average size of 20 to 100 nm and formed of a Eudragit RL-100 or Eudragit RS-100 copolymer, the nanoparticle having a hydrophobic core and a shell having exposed quaternary ammonium groups, and an oxygen sensitive photoluminescent dye embedded in the hydrophobic core, the method comprising the steps of incubating an aqueous suspension of photoluminescent probe typically having a probe concentration of 1 to 10 μg/ml with the live mammalian cell under normal growth conditions at a constant temperature and ideally for a period of time from 30 minutes to 48 hours, wherein the photoluminescent probe is passively loaded in the cell.

The invention also provides a photoluminescent probe composition comprising photoluminescent probe nanoparticles suspended in an aqueous carrier, in which the photo luminescent probe nanoparticle have an average size of from 20 to 100 nm and comprises a polymer matrix formed of a co-polymer of poly (ethylacrylate, methyl-metacrylate and chloro trimethyl-ammoniethyl methacrylate) containing quaternary ammonium groups, the matrix having a hydrophobic core and a shell characterised by the quaternary amino groups, and a hydrophobic oxygen-sensitive photoluminescent dye embedded in the hydrophobic core, wherein the dye is selected from a Pt-porphyrin, Pd-porphyrin, Pt-porphyrin-ketone or Pd-porphyrin-ketone, Pt-benzoporphyrin or Pd-benzoporphyrin, cyclometallated complex of $Ir^{3+}$, $Os^{2+}$ or $Ru^{2+}$, or close analogs or derivatives of these dyes.

Preferably, the co-polymer of poly (ethylacrylate, methyl-metacrylate and chloro trimethyl-ammoniethyl methacrylate) comprises from 8% to 12% of quaternary ammonium groups.

Ideally, the polymer matrix is formed of Eudragit RL-100 polymer containing 0.1-3% w/w of PtPFPP dye.

The invention also relates to a photoluminsecent probe composition of the invention in a dehydrated form (for example, lyophilized for storage).

The invention also relates to a method of forming a photoluminscent probe composition of the invention, the method comprising the steps of dissolving the co-polymer and the hydrophobic oxygen-sensitive photoluminescent dye in acetone, and precipitating the dissolved co-polymer and dye in water to generate a suspension of photoluminescent dye-containing nanoparticles, and subsequent removal of acetone.

BRIEF DESCRIPTION OF FIGURES

The invention will be more clearly understood from the following description of some embodiments thereof, given by example only, and with reference to accompanying figures in which:

FIG. 4.A Toxicity of the NP probe (PtPFPP) in MEF cells.

FIG. 4.B RL100-PtTFPP concentration dependent signal in HCT116 cells loaded for 14 h.

DETAILED DESCRIPTION OF THE INVENTION

The probe of the invention comprises a composition of an amphyphilic cationic polymer and a hydrophobic oxygen-sensitive dye, which is specially processed to produce a suspension of particles having pre-defined characteristics. In particular, the particles have the size in the region of 20-100 nanometers, i.e. much smaller than the size of a typical mammalian cell (~10 microns), typically relatively narrow size distribution, and characteristic core-shell architecture. The hydrophobic core of the nanoparticles is used for impregnating them with hydrophobic oxygen-sensitive dyes (or a combination of several dyes to allow ratiometric $O_2$ sensing), while the hydrophilic shell bears a number of cationic groups (preferably as part of the polymer backbone) on the surface providing strong interaction with the surface of mammalian cells which facilitates efficient loading with the probe.

Examples of polymers that can be used in the invention include poly (ethylacrylate, methyl-methacrylate, and chloro trimethyl-ammonioethyl methacrylate) copolymers having quaternary cationic groups. Examples of such copolymers include Eudragit RL-100 and RS-100 polymers produced by Degussa/Evonic Industries. Thus, Eudragit RL100 is a copolymer of poly (ethylacrylate, methyl-methacrylate, and chloro trimethyl-ammonioethyl methacrylate) containing between 8.8% and 12% of quaternary ammonium groups, M.W. is approximately 150,000 D. Eudragit RS-100 polymer has a similar chemical composition, but contains less quaternary ammonium groups. Some other polymers can also be used, for example sol-gel nanoparticles with the indicator dye embedded inside and the surface modified with quaternary cationic (i.e. ammonium) groups. These polymers can be easily processed to produce the nanoparticle probe of the invention. One such method involves dissolving the polymer and the oxygen-sensitive dye in a medium polarity solvent (e.g. acetone) and subsequent dilution of this solution with water followed by the removal of acetone (Example 1). This method has been successfully applied to produce the RL-100 nanoparticles impregnated with different $O_2$-sensitive dyes, including platinum(II) complexes with octaethylporphyrin (PtOEP), meso-tetra(pentafluorophenyl)porphyrin (PtPFPP), octaethylporphyrin ketone (PtOEPK) and various benzoporphyrins. The resulting nanoparticles had the size of approximately 70 nm, Z-potential of +58 mV, and showed bright phosphorescence in aqueous solution which was quenched by oxygen. Impregnation of RL-100 nanoparticles with perylene and some other hydrophobic fluorescent dyes was also conducted, to mimic the corresponding $O_2$ probes in cell loading and probe localisation studies.

Furthermore, it is demonstrated herein that the oxygen probes having the above characteristic features are highly efficient in loading various mammalian cells by passive means. In one aspect, loading is achieved by simply incubating the cells with the probe under standard culturing conditions (i.e. growth medium, $CO^2$ atmosphere, additives, 37° C.). After the exposure to a relatively low probe concentration (~1-10 µg/ml), relatively high loading of the cells is achieved in 1-6 h, and after 12-24 h the cells produce very high phosphorescent signals. Furthermore, the probes of the invention load efficiently in different cells types (both adherent and suspension), and after loading they remain inside the cell over long periods without significant leaching, and work very reliably and reproducibly. Unlike many other cell-penetrating probes, loading with these probes is not blocked by high serum content in the medium. Such simple and efficient loading of cells and high brightness of the probe make it easy to measure intracellular oxygen by phosphorescence quenching and conduct various physiological experiments with mammalian cells and tissue.

For the latter application, the preferred probe of the invention comprises Eudragit RL-100 nanoparticles impregnated with PtPFPP dye (suitably ~1% w/w), and typically diluted to a working concentration of 1-10 µg/ml in an aqueous solvent. Such probe provides excellent brightness and photostability under intense illumination (important for imaging applications), optimal sensitivity to oxygen, long emission lifetime and convenient spectral properties. It is well compatible with both PMT-based detectors and imaging devices (fluorescent microscopes), and allows phosphorescence lifetime based sensing of oxygen on standard fluorometers, time-resolved fluorescence readers or more sophisticated fluorescence lifetime imaging (FLIM) systems. This probe IS easy to produce and it can be stored over long periods of time without deterioration.

For the sensing of intracellular oxygen and physiological experiments with cells it is important to control the intracellular location of the probe and avoid possible effects of the probe (and assay) on cellular function. Many existing probes suffer from undefined or uncontrolled sub-cellular localisation, transport to undesirable compartments such as cell nucleus, significant intrinsic toxicity and interference with cellular function. We demonstrate in this invention that the self-loading nanoparticle probes show similar localisation pattern in different cell types and low intrinsic toxicity. Thus, in MEF cells the probe penetrates inside, but does not go into the nucleus and localises close to it. Probe localisation pattern resembles that of periplasmic vesicles.

Another aspect of the invention is the method of measuring cellular oxygen concentration using the above probes. The method involves growing test cells, exposing them to the probe for a reasonable period of time under normal culturing conditions to achieve efficient cell loading by passive means. After that the cells are generally normally washed with medium and subject to fluorescence/phosphorescence measurements. The latter is generally conducted under constant temperature (37° C.) and external gas composition (normoxia—21% $O_2$ or hypoxia—reduced atmospheric p $O_2$) by luminescence intensity, lifetime or phase measurements. Measured phosphorescent signal (or signal profile) is converted into $O_2$ concentration using pre-determined calibration of the intracellular probe. The new nanoparticle probes make the assay simple and accurate. The core-shell structure also ideally shield the $O_2$-sensitive dye from interfering specie that may occur in the sample.

In the preferred embodiment the phosphorescent signal from the cells loaded with probe is measured on a sensitive fluorescent reader which supports time-resolved fluorescence or lifetime measurement mode. This allows simple quantification of local oxygen levels within a monolayer of adherent cells or a slice of respiring tissue (i.e. cell population studies), and real-time monitoring of changes in cell respiration and metabolic activity. The sample can also be analysed on a fluorescent microscope to analyse $O_2$ levels in individual cells or sections of a samples.

Another embodiment describes the method of invention in which the intracellular probe contains an additional fluorescent dye which produces a distinct emission. In this case, the $O_2$ sensitive dye produces a photoluminescence intensity signal which is dependent on $O_2$ concentration, whereas the second dye emission is $O_2$-insensitive. Such probe and method allow monitoring of cell oxygenation and metabolic responses by ratiometric intensity measurements. The mode is simpler and more common than phosphorescence lifetime measurements, and supported by many standard microscopes and spectrometers. Examples of such pairs of dyes include PtPFPP and a perylene dye, PtPFPP and a coumarin dye.

The method of invention using the new nanoparticle probes can be used to study the effects of drugs and various stimuli on cell metabolism. This is conducted by preparing the cells, loading them with the nanoparticle probe, washing and equilibrating in the desired medium, temperature and gas composition. Under these conditions probe signal is recorded which corresponds to the respiratory activity of resting cells (basal oxygen concentration). After that the cells are stimulated with a drug or effector added to the sample, and changes in probe signal are recorded. The resulting changes in probe signal, if occur, are indicative to the changes in cell metabolism. Thus, increased probe signal (intensity or lifetime) is indicative to increased respiration activity which lowers intracellular $O_2$ concentration, while decreased probe signal reflects inhibition of respiration which brings cellular $O_2$ levels closer to those of bulk medium. In this application, it is very important to ensure partial deoxygenation of cell microenvironment due to respiration. This can be achieved by optimising the density/numbers, respiratory activity of test cells under resting conditions and/or external $O_2$ levels (hypoxia). Contribution of diffusion processes which influence the shape of the phosphorescent signal (Zhdanov et al.—*Integr. Biol.*, 2010) should be considered.

Overall, compared to the existing conventional $O_2$ probes, including the 'molecular' probes with self-loading capabilities, the nanoparticle $O_2$ probes of the invention have multiple advantages. They are relatively large in size and can be heavily loaded with the dye (up to 3% w/w), thus providing high brightness. The production and impregnation of the probe are simple and allow the use of oxygen-sensitive dyes with different spectral characteristics, chemical structures, including the highly photostable dyes such as PtPFPP. These probes load the cells passively, under mild conditions, with high efficiency and speed, low cell-specificity and minimal impact on cellular function. They have a defined sub-cellular localisation and low intrinsic cyto-, geno- and photo-toxicity. The probes provide simple real-time monitoring of cellular $O_2$ concentration in adherent and suspension cells and responses to stimulation. Large cell populations (monolayers, tissue slices) and individual cells can be analysed.

The invention is demonstrated with the following non-limiting examples.

Example 1. Fabrication of the Nanoparticle $O_2$ Probe 1.5 g of RL-100 polymer and 22.5 mg of PtTFPP were dissolved in 750 g of acetone. The solution was placed in a 5L beaker to which 4 L of deionized water were added over 20 s under rigorous stirring. Acetone was subsequently removed under reduced pressure and aqueous dispersion of the beads was further concentrated to approximately 75 mL. Traces of aggregates were removed by filtration through a paper filter. The resulting solution was filtered through a sterile filter to produce stock of $O_2$ probe for intracellular use. It was aliquoted and stored in a dark place at +4° C. for several months for further use.

Example 2. Assessment and Optimisation of Cell Loading

Mouse embryonic fibroblast (MEF) cells were cultured in 96-well plates using DMEM medium supplemented with 10% of foetal calf serum, $CO_2$ incubator at 37° C., until they reach high confluence (periodically changing medium, if required). Stock solution of the PtPFPP-RL100 probe was diluted to the desired concentration with appropriate growth medium (determined by the cells and culturing conditions) and added to the wells with growing cells at the required final concentration (usually 1-10 µg/ml). Cells were incubated with probe, typically for 6-24 h, and then washed two times with fresh medium. Similar experiments were conducted with other cells, probe concentrations and incubation times. The efficiency of cell loading was assessed by measuring phosphorescence intensity signals in each well on a fluorescent reader Victor2 (Perkin Elmer) in time-resolved mode under the following settings: excitation—340 nm, emission—642 nm, delay time—30 us, gate time—100 us, number of flashes—1000, temperature—37° C. The plate with loaded cells and necessary controls (wells without probe or without cells) was pre-incubated for—15-20 min (to achieve temperature and gas equilibration), and then measured repetitively over 20-30 min taking reading every 2 min.

Similar experiments were conducted on loading the cells with RL100-perylene fluorescent nanoparticles. After incubation with the probe, loaded adherent cells were trypsinised and analysed by flow-cytometry using 488 nm laser and 560 nm emission filter.

Figure 1:
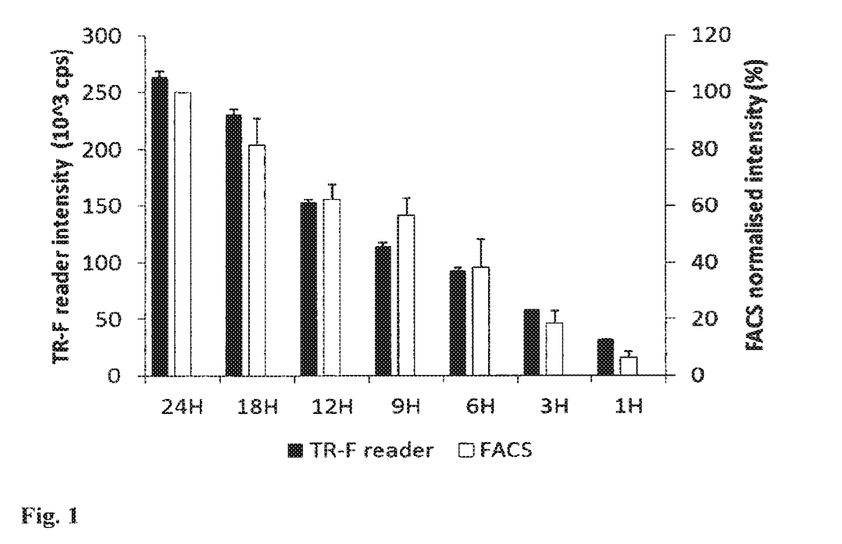
FIG. 1. Loading of the NP probe in MEF cells in (control—24 h).
Figure 2:
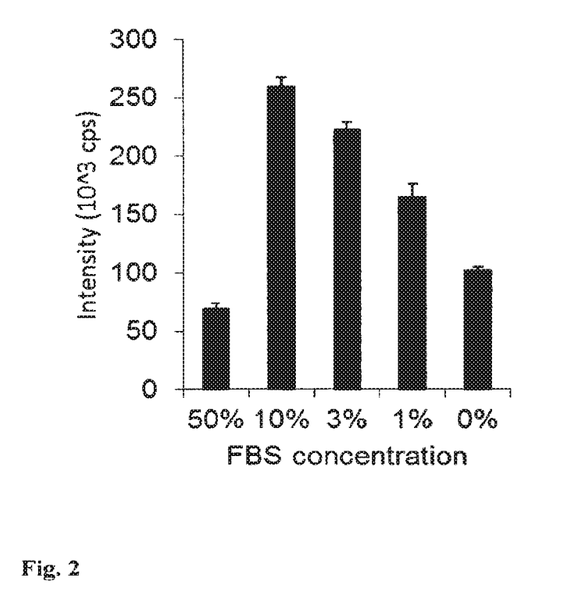
FIG. 2. Effect of serum content on probe loading in HCT116 cells.
Figure 3:
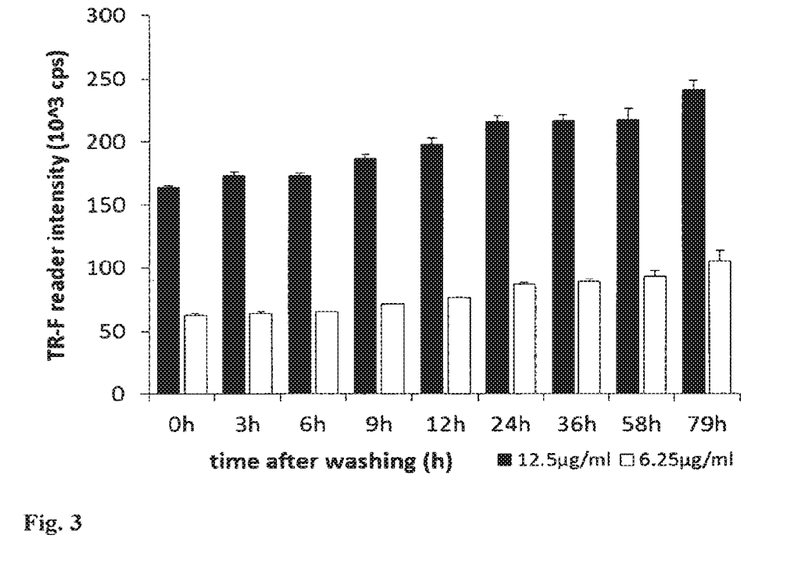
FIG. 3. Signal stability measured in HCT116 cells. Increase in intensity due to cell growth.

FIG. 1 shows that the PtPFPP-RL100 probe provides high and rapid loading, acceptable threshold levels of TR-F intensity signal (~30,000 cps) which allow reliable lifetime based sensing of $O_2$ were achieved even after 1 h. RL100-perylene probe also shows a similar loading pattern as the PtPFPP-RL100 probe (measured by flow cytometry). Loading in media with high serum content remains pretty good (FIG. 2), and signal intensity remains high over 72 h for PtPFPP-RL100 probe loaded HCT116 cells—(FIG. 3). Therefore, the probe can be used in long-term experiments with cells.

Example 3. Analysis of Probe Cytotoxicity and Localisation

Figure 4A:
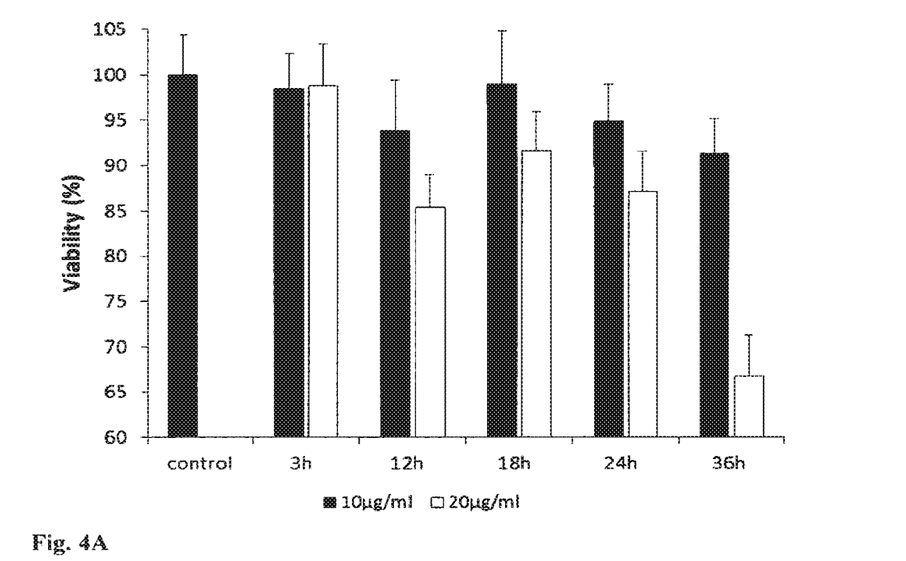
Figure 4B:
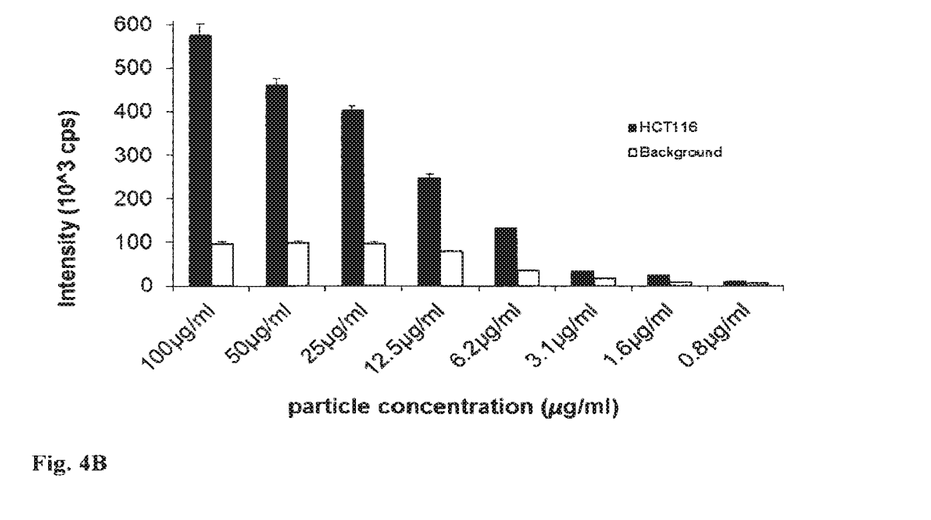

MEF, PC12, HepG2 and HCT116 cells were loaded with 10 μg/ml of PtPFPP-RL100 probe as described in Example 2. Probe cytotoxicity was assessed by measuring total ATP levels in loaded cells and comparing them with unloaded cells. FIG. 4A shows that the probe has low intrinsic toxicity, particularly when used at low concentrations (10 μg/ml) and short loading times (<18 h). FIG. 4B shows the concentration dependence of specific signal from HCT116 cells loaded with R1100-PtTFPP for 14 h and background (non-specific binding to plate). Concentrations higher than 25 ug/ml had a toxic effect on cells.

Figure 5:
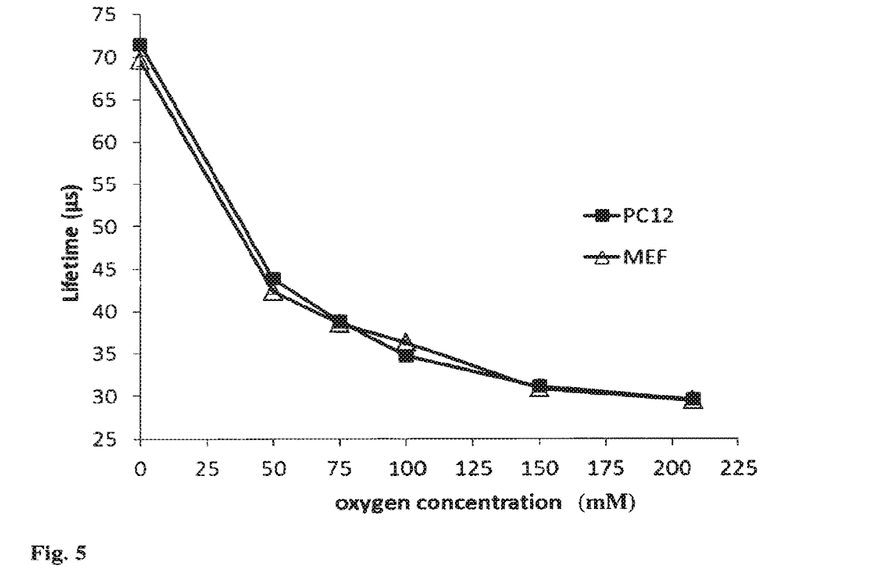
FIG. 5. Probe calibrations in different cell lines measured by time-resolved fluorometry.

Example 4. Calibration of the Nanoparticle Probe for the Quantification of Intracellular $O_2$ Concentration MEF, PC12, HepG2 and HCT116 cells were grown in standard 96-well plates in growth medium containing 10% FBS, and then loaded with PtPFPP-RL100 probe as described in Example 2 (10 μg/ml, 12 h). TR-F reader Victor3 on which the measurements were carried out was placed in a hypoxia chamber (Coy Scientific) pre-set at constant $pO_2$ (ranging between 0 and 21%). Antimycin A was added to the wells with loaded cells (to block their respiration and formation of local $O_2$ gradients in the wells), and the plate was then placed in the reader compartment. After a period of temperature and gas equilibration (20-40 min) the plate was measured repetitively over a period of 20-40 min, taking TR-F intensity values at two different delay times (30 us and 70 us, respectively) which were used to calculate the phosphorescence lifetime. After the measurements were completed, the hypoxia chamber was reset to a new $pO_2$ value and the cycle (equilibration and measurement) was repeated. Kinetic profiles of phosphorescence lifetime of the probe were processed to determine average values at different external $pO_2$. These values were used to construct probe calibration which is shown for MEF and PC12 in FIG. 5. This calibration can be used to determine $O_2$ levels in respiring cells, both at rest and upon stimulation.

Example 5. Monitoring Cellular Responses to Metabolic Stimulation

Figure 6:
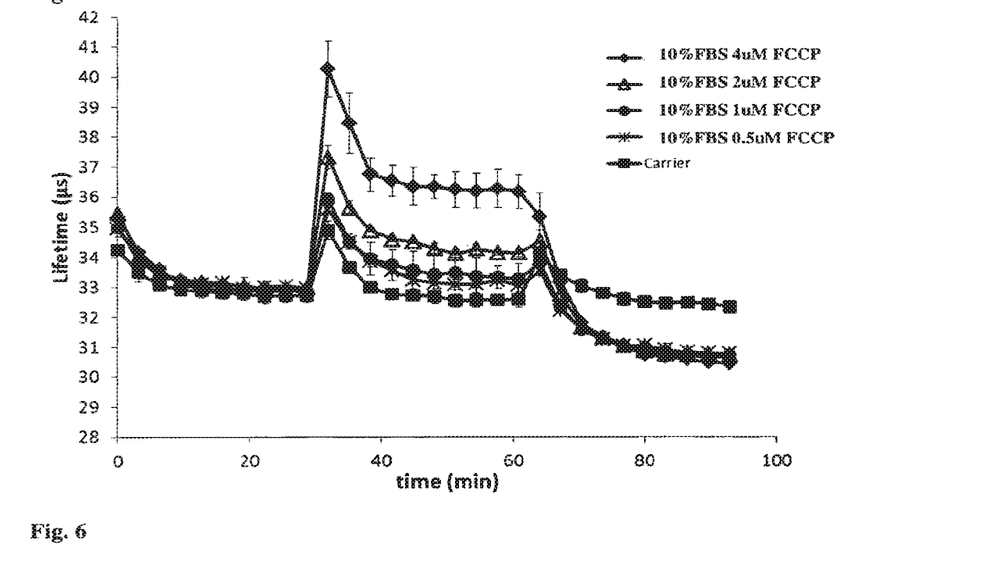
FIG. 6. Metabolic responses of MEF cells to different concentrations of the mitochondrial uncoupler (FCCP), measured with the PtPFPP-RL100 probe (10 ug/ml, 12 h loading, DMEM).

MEF cells were cultured in a standard 96-well plate, (typically 24-36 wells, 20,000 cells/well) in DMEM medium, loaded with the nanoparticle $O_2$ probe as described (10 ug/ml, 12 hours), washed 2 times and covered with 90 uL of medium. The plate was then measured on a Victor 2 reader as described in Example 4. Initially it was monitored for ~30 min to reach $O_2$ and temperature equilibrium and obtain basal signals, then quickly withdrawn from the reader, compounds were added to the cells (10 ul of 10× stock solution in each well) and monitoring was resumed. Measured TR-F intensity signals for each sample well were converted into phosphorescence lifetime (t) values and plotted. Control samples and repetitive additions were incorporated as appropriate. FIG. 6 shows the responses to stimulation with different concentrations of uncoupler FCCP (added at 30 min, which is known to increase cellular respiration. Increases in probe lifetime reflect (in real time) the reductions in cellular $O_2$ levels due to increased respiration.

The invention is not limited to the embodiments hereinbefore described which may be varied in construction and detail without departing from the spirit of the invention.

The invention claimed is:

1. A method of determining oxygen concentration in a live mammalian cell sample by photoluminescence quenching technique, which method employs a photoluminescent probe, the method comprising:
    incubating the live mammalian cell sample in a suitable growth medium with the photoluminescent probe capable of self-loading sans any loading reagent into the cells of the mammalian cell sample;
    detecting a photoluminescent signal of the photoluminescent probe from the probe-loaded cell sample; and
    correlating the detected photoluminescent signal to local oxygen concentration within the live mammalian cell sample,
    wherein the photoluminescent probe is a plurality of polymeric particles each comprising an amphiphilic cationic polymer matrix having a hydrophobic core and a hydrophilic positively charged surface provided by quaternary amino groups, and a hydrophobic oxygen-sensitive photoluminescent dye embedded in the hydrophobic core,
    wherein the photoluminescent probe is a Pt-tetrakis (pentafluorophenyl) porphine (PtPFPP)-Poly (ethyl acrylate-co-methyl methacrylate-co-trimethylammonioethyl methacrylate chloride) probe, and wherein the PtPFPP-Poly (ethyl acrylate-co-methyl methacrylate-co-trimethylammonioethyl methacrylate chloride) probe comprises the PtPFPP as a hydrophobic oxygen sensitive photoluminescent dye and the Poly (ethyl acrylate-co-methyl methacrylate-co-trimethylammonioethyl methacrylate chloride) as an amphiphilic cationic polymer.

2. The method of claim 1, wherein the photoluminescent probe is in the form of an aqueous suspension of nanoparticles at a working concentration of 0.1 to 100 μg/ml.

3. The method of claim 1, wherein the photoluminescent probe has low intrinsic toxicity on the cells.

4. The method of claim 1, wherein the photoluminescent probe is capable of 1.5 to 15 fold quenching at ambient oxygen concentration of 21 kPa or 250 μM O2.

5. The method of claim 1, wherein the cell sample is washed prior to measurement of the photoluminescent signal to remove extracellular probe.

6. The method of claim 1, wherein the photoluminescent signal is detected by time-resolved fluorometry in the microsecond domain.

7. The method of claim 1, wherein the photoluminescent signal is detected by fluorescence microscopy imaging technique.

8. The method of claim 1, wherein detecting the photoluminescent signal includes measuring the photoluminescence lifetime of the photoluminescent signal or a parameter related to it.

9. The method of claim 1, wherein the photoluminescent signal is detected using ratiometric intensity based oxygen sensing or imaging and the photoluminescent probe further contains an oxygen-insensitive dye which is used as a reference or as part of a FRET pair.

10. A method of determining the metabolic activity of a cell or a cell population, wherein the method comprises monitoring oxygen concentration of the cell or cell population by:
    incubating the cell or cell population in a suitable growth medium with a photoluminescent probe capable of self-loading sans any loading reagent into the cell or cells of the cell population;
    detecting a photoluminescent signal of the photoluminescent probe from the probe-loaded cell or cell population;
    correlating the detected photoluminescent signal to local oxygen concentration within the cell or cell population, and
    correlating the measured oxygen concentration, or changes in the oxygen concentration, of the cell or cell population to metabolic activity of the cell or cell population,
    wherein the photoluminescent probe is a plurality of polymeric particles each comprising an amphiphilic cationic polymer matrix having a hydrophobic core and a hydrophilic positively charged surface provided by quaternary amino groups, and a hydrophobic oxygen-sensitive photoluminescent dye embedded in the hydrophobic core,
    wherein the photoluminescent probe is a Pt-tetrakis (pentafluorophenyl) porphine (PtPFPP)-Poly (ethyl acrylate-co-methyl methacrylate-co-trimethylammonioethyl methacrylate chloride) probe, and wherein the PtPFPP-Poly (ethyl acrylate-co-methyl methacrylate-co-trimethylammonioethyl methacrylate chloride) probe comprises the PtPFPP as a hydrophobic oxygen sensitive photoluminescent dye and the Poly (ethyl acrylate-co-methyl methacrylate-co-trimethylammonioethyl methacrylate chloride) as an amphiphilic cationic polymer.

11. A method of determining the effects of a test substance on the metabolic activity of a cell or cell population, the method comprising stimulating the cell or cell population with the test substance and determining the metabolic activity of the cell or cell population by:
    incubating the cell or cell population in a suitable growth medium with a photoluminescent probe capable of self-loading sans any loading reagent into the cell or cells of the cell population;
    detecting a photoluminescent signal of the photoluminescent probe from the probe-loaded cell or cell population using ratiometric intensity based oxygen sensing or imaging;
    correlating the detected photoluminescent signal to local oxygen concentration within the cell or cell population, and
    correlating the measured oxygen concentration, or changes in the oxygen concentration, of the cell or cell population to metabolic activity of the cell or cell population,
    wherein the photoluminescent probe contains an oxygen-insensitive dye which is used as a reference or as part of a FRET pair, the photoluminescent probe being a plurality of polymeric particles each comprising an amphiphilic cationic polymer matrix having a hydrophobic core and a hydrophilic positively charged surface provided by quaternary amino groups, and a hydrophobic oxygen-sensitive photoluminescent dye embedded in the hydrophobic core,
    wherein the photoluminescent probe is a Pt-tetrakis (pentafluorophenyl) porphine (PtPFPP)-Poly (ethyl acrylate-co-methyl methacrylate-co-trimethylammonioethyl methacrylate chloride) probe, and wherein the PtPFPP-Poly (ethyl acrylate-co-methyl methacrylate-co-trimethylammonioethyl methacrylate chloride) probe comprises the PtPFPP as a hydrophobic oxygen sensitive photoluminescent dye and the Poly (ethyl acrylate-co-methyl methacrylate-co-trimethylammonioethyl methacrylate chloride) as an amphiphilic cationic polymer.

* * * * *